United States Patent
Kuyler et al.

(10) Patent No.: US 11,234,712 B2
(45) Date of Patent: Feb. 1, 2022

(54) MEDICAL ACCESS DEVICE

(71) Applicant: Warsaw Orthopedic, Inc., Warsaw, IN (US)

(72) Inventors: Adriaan J. Kuyler, Germantown, TN (US); Benjamin D. Cowan, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 200 days.

(21) Appl. No.: 16/663,855

(22) Filed: Oct. 25, 2019

(65) Prior Publication Data

US 2021/0121185 A1    Apr. 29, 2021

(51) Int. Cl.
*A61B 17/16* (2006.01)

(52) U.S. Cl.
CPC ...... *A61B 17/1604* (2013.01); *A61B 17/1671* (2013.01)

(58) Field of Classification Search
CPC ............ A61B 17/1604; A61B 17/1631; A61B 17/1671; A61B 17/8819
See application file for complete search history.

(56) References Cited

U.S. PATENT DOCUMENTS

| | | |
|---|---|---|
| 781,947 A | 2/1905 | Hartley et al. |
| 783,749 A | 2/1905 | Hartley et al. |
| 789,520 A | 5/1905 | Adell et al. |
| 797,824 A | 8/1905 | Seitz |
| 833,712 A | 10/1906 | Geisenhoner |
| 889,409 A | 6/1908 | Saplding |
| 893,206 A | 7/1908 | Stewart |
| 913,677 A | 3/1909 | Ainsworth |
| 1,008,226 A | 11/1911 | Walin |
| 1,152,890 A | 9/1915 | Gaydosh |
| 1,198,486 A | 9/1916 | Standish |
| 1,341,373 A | 5/1920 | Komatar |
| 1,449,136 A | 3/1923 | Yates |
| 1,458,961 A | 6/1923 | Williams |
| 1,572,046 A | 2/1926 | Seiler |
| 2,384,707 A | 9/1945 | Sweet |
| 2,446,848 A | 8/1948 | Prester |
| 2,455,577 A | 12/1948 | Hager |
| 2,460,113 A | 1/1949 | Young |
| 2,528,383 A | 10/1950 | Mihalik |
| 2,602,360 A | 7/1952 | Berninger |
| 2,762,435 A | 9/1956 | Morris et al. |
| 3,172,204 A | 3/1965 | Frey |

(Continued)

*Primary Examiner* — Samuel S Hanna
(74) *Attorney, Agent, or Firm* — Fox Rothschild LLP

(57) ABSTRACT

A surgical device is provided. The surgical device includes a tubular outer shaft having a longitudinal axis and an angled guide positioned on a first end of the surgical device. The angled guide may be angled relative to the longitudinal axis of the outer shaft. The surgical device includes an elongated inner shaft having a second end and a third end. The inner shaft is removably coupled to the outer shaft and configured to axially translate through the outer shaft. The surgical device includes pivotal device having at least one joint and an access tool. The at least one joint may be pivotally coupled to the third end of the inner shaft and to an end of the access tool. The pivotal device may be configured to axially translate through the angled guide into a deployed position.

12 Claims, 10 Drawing Sheets

(56) References Cited

U.S. PATENT DOCUMENTS

| | | | |
|---|---|---|---|
| 3,177,952 A | 4/1965 | West | |
| 3,230,631 A | 1/1966 | Skidmore | |
| 4,577,400 A | 3/1986 | Morgan | |
| 4,823,468 A | 4/1989 | Kollegger | |
| 4,867,158 A | 9/1989 | Sugg | |
| 5,957,946 A | 9/1999 | Shuler et al. | |
| 6,223,441 B1 | 5/2001 | Parsons | |
| 6,418,628 B1 | 7/2002 | Steingass | |
| 6,960,214 B2 | 11/2005 | Burkinshaw | |
| 7,338,494 B2 | 3/2008 | Ryan | |
| 8,418,781 B2 | 4/2013 | Chambers et al. | |
| 8,740,983 B1 * | 6/2014 | Arnold | A61B 17/8875 |
| | | | 623/17.16 |
| 8,956,377 B2 | 2/2015 | Khalapyan | |
| 9,339,321 B2 | 5/2016 | Stoll et al. | |
| 9,398,918 B2 | 7/2016 | Torrie | |
| 9,763,675 B2 | 9/2017 | Stoll et al. | |
| 9,808,264 B2 | 11/2017 | Estes et al. | |
| 9,968,365 B2 | 5/2018 | Torrie | |
| 2004/0147932 A1 | 7/2004 | Burkinshaw et al. | |
| 2004/0154171 A1 | 8/2004 | Utz et al. | |
| 2008/0243126 A1 | 10/2008 | Gutierrez et al. | |
| 2012/0071876 A1 | 3/2012 | Stoll et al. | |
| 2018/0021047 A1 | 1/2018 | Stoll et al. | |

* cited by examiner

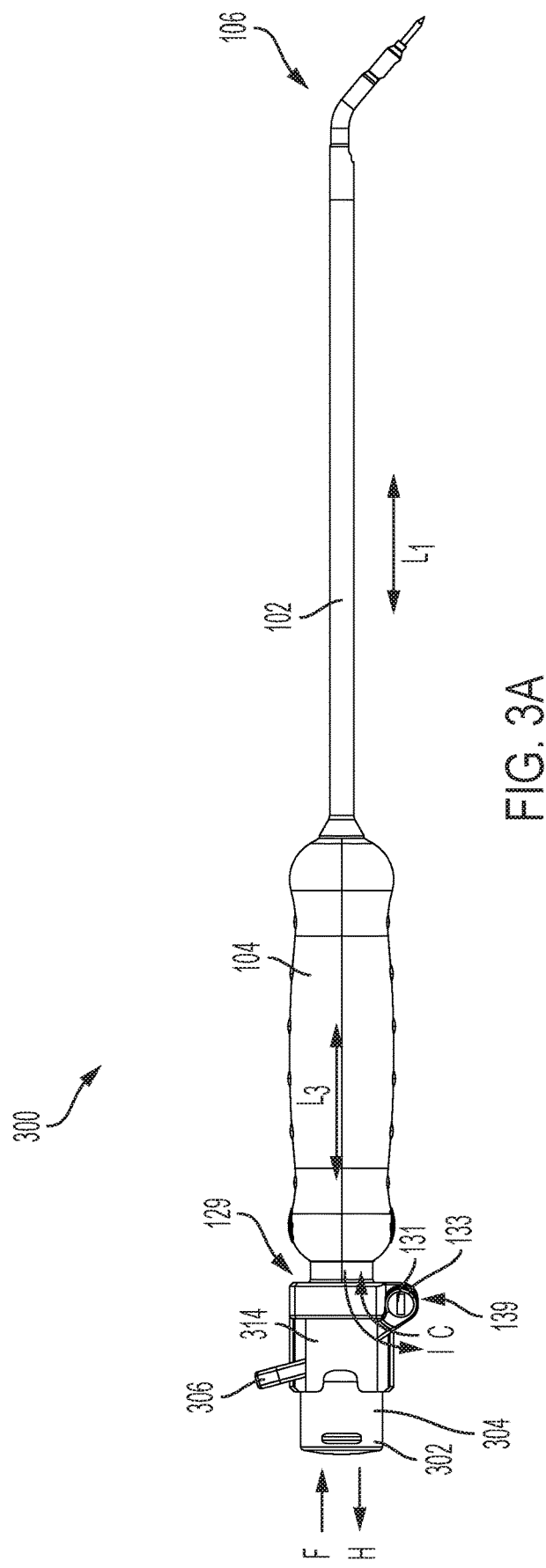

MEDICAL ACCESS DEVICE

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease, and degenerative conditions caused by injury and aging. Spinal disorders typically result in symptoms including pain, nerve damage, and partial or complete loss of mobility.

Non-surgical treatments, such as medication, rehabilitation and exercise can be effective; however, these treatments may fail to relieve the symptoms associated with these disorders. Surgical treatment of these spinal disorders may include correction, fusion, fixation, discectomy, laminectomy, and insertion of implantable prosthetics. As part of these surgical treatments, implants, such as intervertebral fusion implant devices, are often used to fuse two adjacent vertebrae. The intervertebral fusion implant devices may be fixed to one or both adjacent vertebrae and fastened to the vertebra, via bone fasteners inserted through a respective fastener hole of the implant.

To fasten the implant to the vertebra, a user may use an awl medical device to create a hole in the vertebra or other bony structure to insert the fastener or another medical implant or to obtain access into or through a bone. However, certain conventional awls are substantially linear. Thus, certain linear awls may not be able to access a fastener hole of the implant, as the fastener hole may be positioned at an angle that is obstructed by other bodily objects within the patient. Moreover, for the cases in which the tip of the awl is angled, the user cannot strike the linear portion of the awl and create at hole at the angle of the awl tip without the risk of bending or damaging the tip of the awl or for other reasons.

SUMMARY

The present disclosure generally relates to medical devices for the treatment of musculoskeletal disorders, and more particularly, to medical insertion devices.

In one or more cases, the disclosed technology relates to a surgical device. In one or more cases, the surgical device includes a tubular outer shaft having a longitudinal axis and an angled guide positioned on a first end of the surgical device. In one or more cases, the angled guide is angled relative to the longitudinal axis of the outer shaft. In one or more cases, the surgical device includes an elongated inner shaft having a second end and a third end. In one or more cases, the inner shaft is removably coupled to the outer shaft and configured to axially translate through the outer shaft. In one or more cases, the surgical device includes a pivotal device having at least one joint and an access tool. In one or more cases, the at least one joint is pivotally coupled to the third end of the inner shaft and to an end of the access tool. In one or more cases, the pivotal device is configured to axially translate through the angled guide into a deployed position.

In one or more cases, the disclosed technology relates to a surgical device. In one or more cases, the surgical device includes a tubular outer shaft having a longitudinal axis in which an angled guide is positioned on a first end of the surgical device and a housing is positioned on a second end of the surgical device opposite the first end. In one or more cases, the angled guide is angled relative to the longitudinal axis of the outer shaft. In one or more cases, the surgical device includes an elongated inner shaft having a third end and a fourth end. In one or more cases, the inner shaft is removably coupled to the outer shaft and configured to axially translate through the outer shaft. In one or more cases, the surgical device includes a pivotal device having at least one joint and an access tool. In one or more cases, the at least one joint is pivotally coupled to the fourth end of the inner shaft and to an end of the access tool. In one or more cases, the pivotal device is configured to axially translate through the angled guide into a deployed position. In one or more cases, the surgical device includes a knob disposed on the third end of the inner shaft. In one or more cases, the surgical device includes at least one pin protruding from an outer surface of the knob. In one or more cases, the surgical device includes at least one track positioned within the housing and configured to guide the at least one pin as the knob axially translates within the housing. In one or more cases, the surgical device includes an external lever having at least one end pivotally coupled to an outer surface of the housing and at least one slot removably coupled to the pin, thereby securing the inner shaft to the outer shaft.

In one or more cases, the disclosed technology relates to a surgical device. In one or more cases, the surgical device includes a tubular outer shaft having a longitudinal axis in which an angled guide is positioned on a first end of the surgical device and a housing is positioned on a second end of the surgical device opposite the first end. In one or more cases, the angled guide is angled relative to the longitudinal axis of the outer shaft. In one or more cases, the surgical device includes an elongated inner shaft having a third end and a fourth end. In one or more cases, the inner shaft is removably coupled to the outer shaft and configured to axially translate through the outer shaft. In one or more cases, the surgical device includes a pivotal device having at least one joint and an access tool. In one or more cases, the at least one joint is pivotally coupled to the fourth end of the inner shaft. In one or more cases, the pivotal device is configured to axially translate through the angled guide into a deployed position. In one or more cases, the surgical device includes an internal lever pivotally coupled to an outer surface of the housing and having a pin extending transversely from one arm of the internal lever to an opposite arm of the internal lever. In one or more cases, the knob includes a slot removably coupled the pin of the internal lever, thereby securing the inner shaft to the outer shaft.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 3A illustrates a perspective view of another medical access device.

DETAILED DESCRIPTION

Figure 1A:
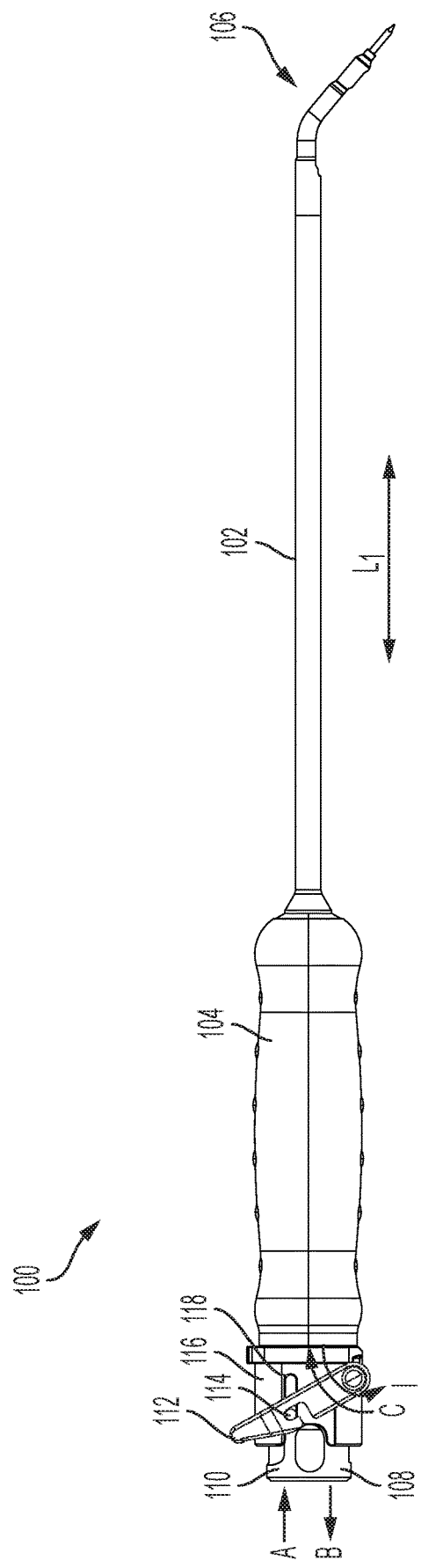
FIG. 1A illustrates a perspective view of an example medical access device.

The following discussion omits or only briefly describes certain conventional features related to medical access devices, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally medical devices for the treatment of musculoskeletal disorders, and more particularly, to medical access devices. Embodiments of the present disclosure are described below with reference to the figures.

Figure 1B:
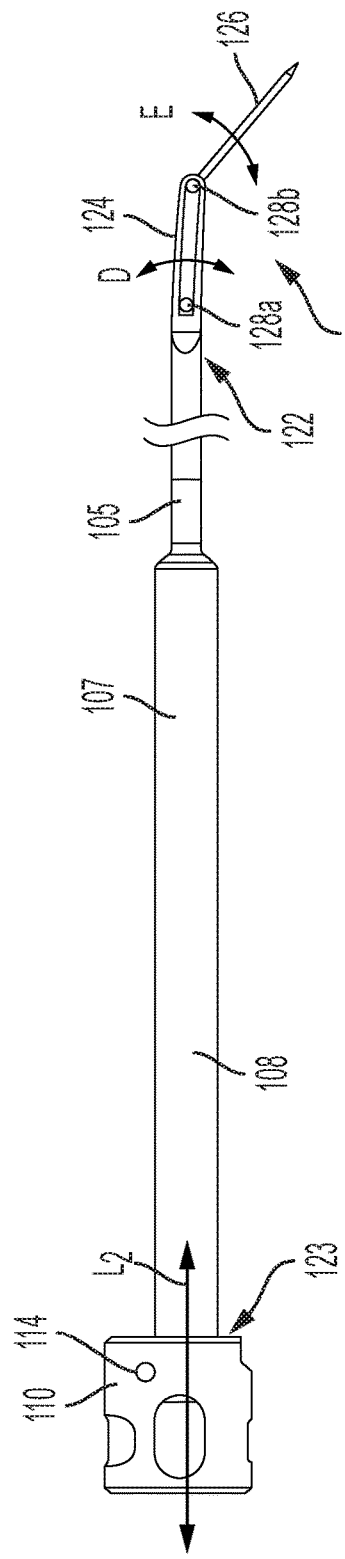
FIG. 1B illustrates a perspective view of an inner shaft of the example medical access device of FIG. 1A.
Figure 1C:
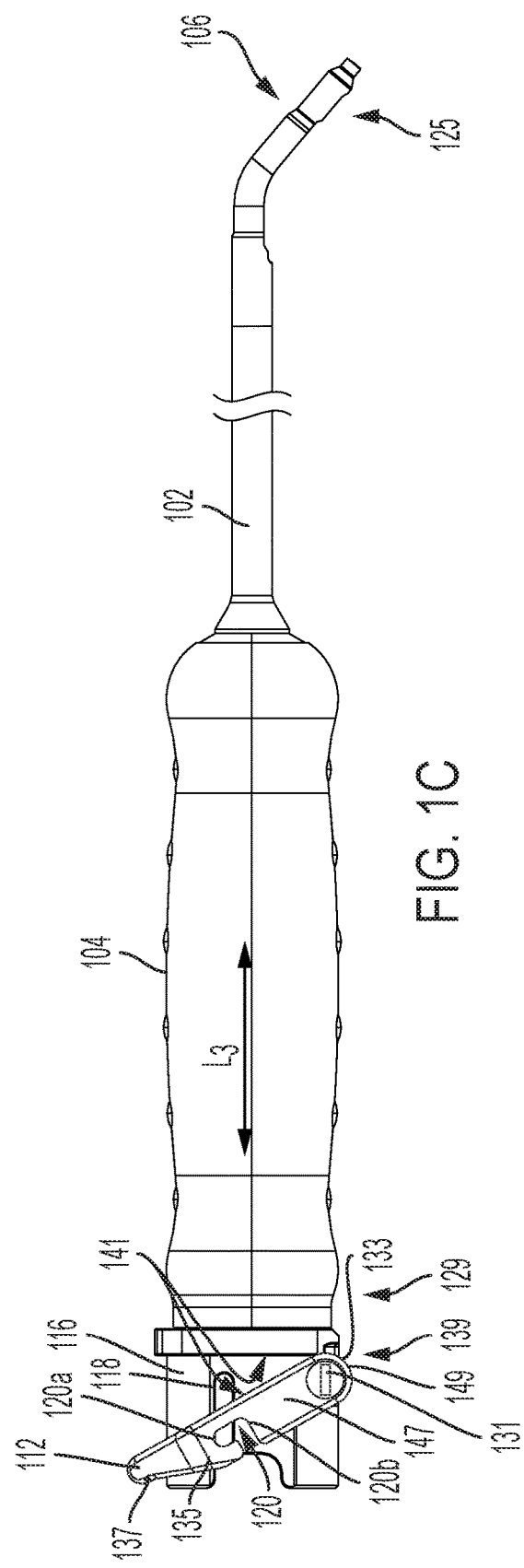
FIG. 1C illustrates a perspective view of an outer shaft of the medical access device of FIG. 1A.

FIG. 1A illustrates a perspective view of an example medical access device 100. FIG. 1B illustrates a perspective view of an inner shaft 108 of the example medical access device 100 of FIG. 1A. FIG. 1C illustrates a perspective view of an outer shaft 102 of the medical access device 100 of FIG. 1A.

In one or more cases, the medical access device 100 (hereinafter the "device 100") may be employed, for example, with an open or mini-open, minimal access and/or minimally invasive technique including, for example, a percutaneous surgical technique to create an access hole for a fastener at a surgical site within a body, for example, a section of a spine of a patient.

The device 100 includes an outer shaft 102 configured to receive an inner shaft 108. The inner shaft 108 may positioned within the outer shaft 102, and may be configured to translate through the outer shaft 102 along an axis $L_1$.

The inner shaft 108 may be an elongated rigid member having a solid center disposed between a first end and a second end 123. The elongated rigid member may be a cylindrical shaft. In one or more cases, the inner shaft 108 is an elongated rigid member having a first portion 107 and second portion 105, in which the diameter of the first portion 107 is greater than the diameter of the second portion 105. The first portion 107 may be configured to be positioned within the handle 104 of the outer shaft 102. For example, the first portion 107 may include a keyed portion configured to interface with a keyed portion formed within the inner surface of the handle 104. The keyed portion of the first portion 107 may include, for example, a flat surface recessed from the diameter of the first portion 107, and the keyed portion of the handle 104 may be a protrusion having a flat surface that protrudes from the inner surface of the handle 104 and is configured to interface with the keyed portion of the first portion 107. The first portion 107 may be configured to withstand the impact of a strike from on object, such as a mallet, on the knob 110 of the inner shaft 108. The smaller diameter of the second portion 105 may be utilized to provide a minimally invasive percutaneous surgical technique. In one or more other cases, the inner shaft 108 includes a uniform diameter extending from the first end 122 and the second end 123.

Figure 4A:
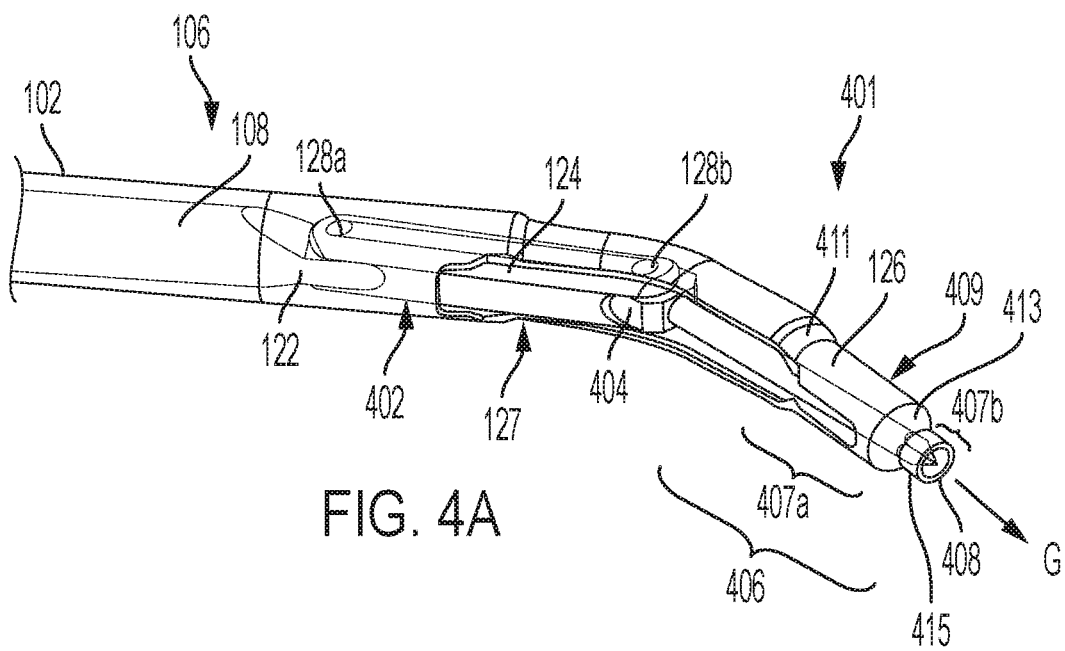
FIG. 4A illustrates the medical access device of FIG. 1A in a retracted position.
Figure 4B:
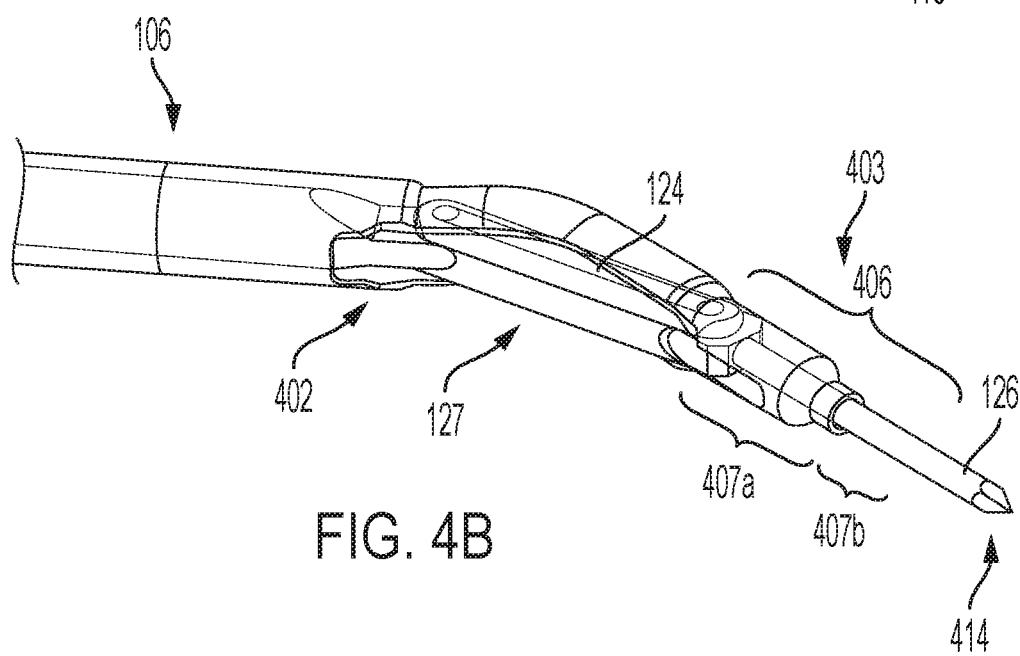
FIG. 4B illustrates the medical access device of FIG. 1A in a deployed position.

The first end 122 of the inner shaft 108 may be pivotally coupled to pivotal device 127. The pivotal device 127 may be employed, for example but not limited to, to create an access hole within a section of spine or other bony structure of a patient. In one or more cases, the access hole may be used to insert the fastener or another medical implant therein, or to obtain access into or through a bone. The pivotal device 127 may include at least one joint, such as a joint 124, and an access tool 126, in which the access tool 126, such as an awl tip, is pivotally coupled to an end 128b of the joint 124, and an opposite end 128a of the joint 124 is pivotally coupled to the first end 122 of the inner shaft 108. For example, the access tool 126 may In one or more cases, the joint 124 may be formed in an "H" shape, such that one end 404 of the access tool 126 fits between the end 128b having one recessed portion of the H-shaped joint 124 and the first end 122 of the inner shaft 108 fits between the end 128a having the other recessed portion of the H-shaped joint 124, as shown in FIGS. 4A and 4B. A pin, for example, but not limited to, a slip fit pin, may be inserted through holes formed on the proximal ends of the recessed portion of the end 128b of the H-shaped joint 124 and a hole formed in the end 404 of the access tool 126, in which the holes of the recessed portion and the end 404 align with one another. The pin may be welded on each side of the recessed portion, thereby coupling the access tool 126 to the joint 124. It should be noted that the end 128a of the joint 124 may be coupled to the first end 122 of the inner shaft 108 in a same or similar manner as the end 128b of the joint 124 coupled to the access tool 126. In one or more other cases, the end 404 of the access tool 126 may have a "U" shaped end, in which the end 128b of the joint 124 fits between the U-shaped end 404 of the access tool 126. The first end 122 of the inner shaft 108 may also have a "U" shaped end, in which the end 128a of the joint 124 fits between the U-shaped first end 122 of the inner shaft 102. For the cases in which the pivotal device 127 utilizes more than one joint, each joint may be connected in sequence, in which an end of the first joint connects to the first end 122 of the inner shaft 108, and an end of the last joint in the chain of joints connects to the end 404 of the access tool 126. In one or more cases, the joint 124 may rotate 180° about the inner shaft 108. In one or more cases, the access tool 126 may rotate 180° about the joint 124. In one or more other cases, the range of rotation of the joint 124 may be limited with respect to the inner shaft 108. For example, the joint 124 may be limited to rotate 90° about the inner shaft 108. In one or more other cases, the range of rotation of the access tool 126 may be limited with respect to the joint 124. For example, the joint 124 may be limited to rotate 90° about the joint 124.

In one or more cases, the joint 124 may rotate in a direction D within a range of 180 degrees or about 180 degrees with respect to the first end 122. In one or more cases, the access tool 126 may rotate in a direction E within a range of 180 degrees or about 180 degrees with respect to the joint 124. In one or more other cases, the joint 124 and/or the access tool 126 may be limited to rotate in one direction, for example to a right of the inner shaft 108 or to a left of the inner shaft 108.

Figure 6A:
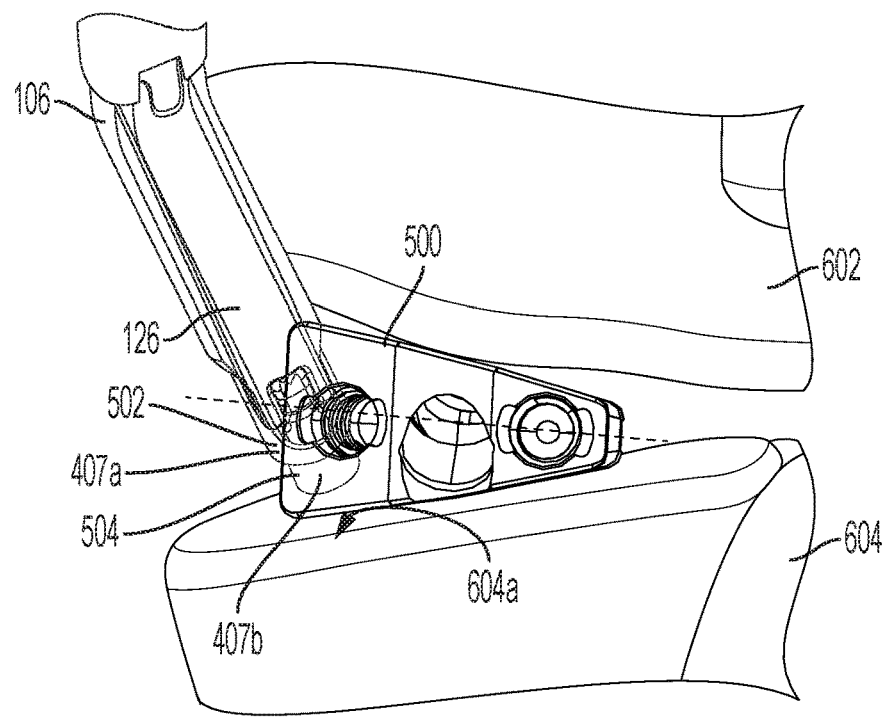
FIG. 6A illustrates a medical access device positioned within the medical implant of FIG. 5 in a retracted positioned.
Figure 6B:
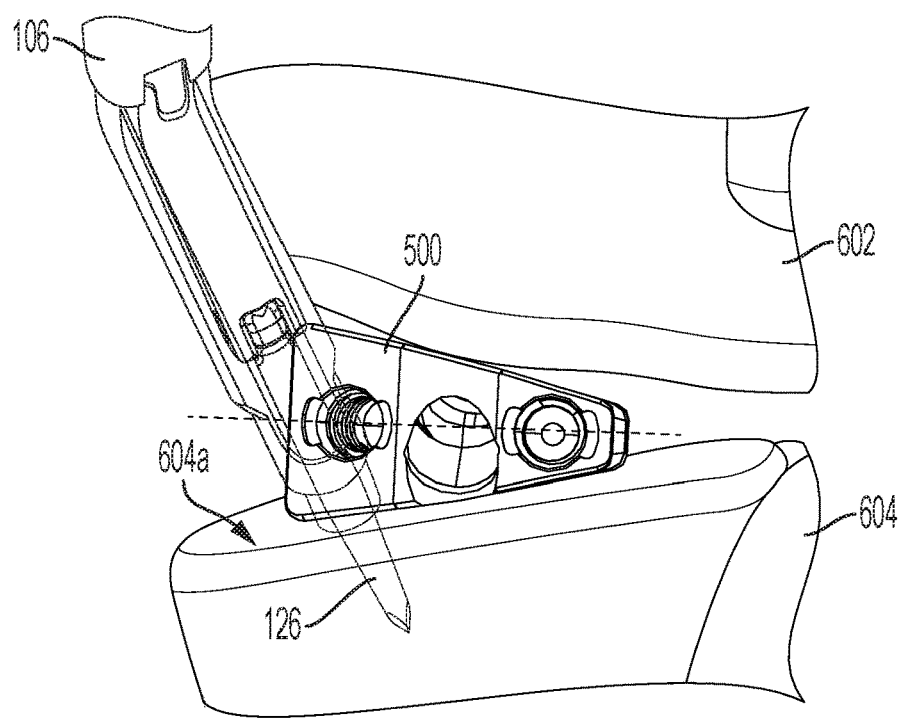
FIG. 6B illustrates a medical access device positioned within the medical implant of FIG. 5 in a deployed positioned.

The second end 123 of the inner shaft 108 may be fixedly coupled to the knob 110. In one or more cases, the knob 110 may be fixedly coupled to the second end 123, via fastening the knob 110 to the second end 123 of the inner shaft 108 with a fastener, such as a screw; welding the knob 110 to the second end 123 or the like. The upper surface 134 of the knob 110 may be a flat surface configured to receive one or more strikes from another object, such as a mallet, hammer, or other like instruments. The knob 110 may translate the force from the strike to the pivotal device 127 and into another object such as a vertebra 604, as shown in FIG. 6B. That is, the device 100 may translated the linear force from the strike on the knob 110 into an angular force when the pivotal device 127 is inserted into another object at an angle. The force from the strike may also cause the inner shaft 108 to move through the outer shaft 102. In a fully deployed position 403, the upper surface 134 may be elevated by a distance 130 from the upper surface 132 of the outer housing 116. By having the upper surface 134 elevated from the upper surface 132 in a fully deployed position 403, the object, such as the mallet, is prevented from contacting the upper surface 132 and translating the force of the strike into the outer shaft 102.

The knob 110 may include one or more pins, such as pin 114, which protrude from the outer surface of the knob 110. In one or more cases, the pins 114 may be positioned center with the central axis $L_2$ of the knob 110, or may be positioned off-center with the central axis $L_2$ of the knob 110. The pins 114 may be positioned centered or off-centered for the cases in which the access tool 126 and the joint 124 are each configured to rotate within a range of 180 degrees or about 180 degrees. In one or more other cases, in which the rotation of the pivotal device 127 is limited to rotate in one direction, the pins 114 may be positioned off-center from the central axis $L_2$ of the knob 110. By positioning the pins 114 off-center from the central axis $L_2$, the knob 110 may only be inserted into the outer housing 116 of the outer shaft 102 in one configuration, thereby preventing a user from improperly installing the inner shaft 108 within the outer shaft 102.

The outer shaft 102 may be an elongated rigid member having a hollow center disposed between a first end 125 and a second end 129. An angled guide 106 may be disposed on the first end 125 of the outer shaft 102, opposite the second end 129. The angled guide 106 may house and provide a protective covering for the pivotal device 127. The angled guide 106 may provide an angled pathway in a direction G, as the pivotal device 127 moves from a retracted position 401, as shown in FIG. 4A, to a deployed position 403, as shown in FIG. 4B, and vice versa. In one or more cases, the angled guide 106 may be angled, with respect to the central axis $L_3$ of the outer shaft 102, between 0 degrees and 90 degrees, preferably 20 degrees and 70 degrees, and more preferably be angled at 45 degrees or about 45 degrees. In one or more other cases, the angled guide 106 may be angled to correspond to the angle of a receptacle 501 of a medical implant 500.

Figure 4C:
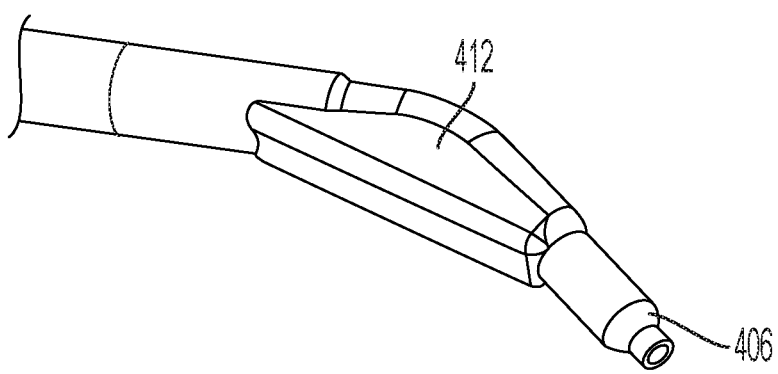
FIG. 4C illustrates a guide expansion area for the medical access device of FIG. 1A.

In one or more cases, the angled guide 106 includes a guide expansion area configured to provide the pivotal device 127, and in particular, the joint 124, room to turn, as the pivotal device 127 moves from a retracted position 401 to a deployed position 403, and vice versa. In one or more cases, the guide expansion area 402 may be a removed section of the angled guide 106, as shown in FIGS. 4A and 4B. The guide expansion area 402 may be an opening that exposes the inner shaft 108 to an outside environment. At the guide expansion area 402, the pivotal device 127 may extend beyond the angled pathway of the angled guide 106, as shown in FIG. 4B, allowing the pivotal device 127 to turn in the angled guide 106. In one or more other cases, the guide expansion area 412 may be an enclosed rigid protrusion formed by the outer shaft 102, as shown in FIG. 4C. At the guide expansion area 412, the inner shaft 108 may not be exposed to the outside environment. The guide expansion area 412 may protrude inwardly from the angled guide 106, such that the guide expansion area 412 is angled, with respect to the central axis $L_3$ of the outer shaft 102, at a different angle than the angled guide 106.

Figure 5:
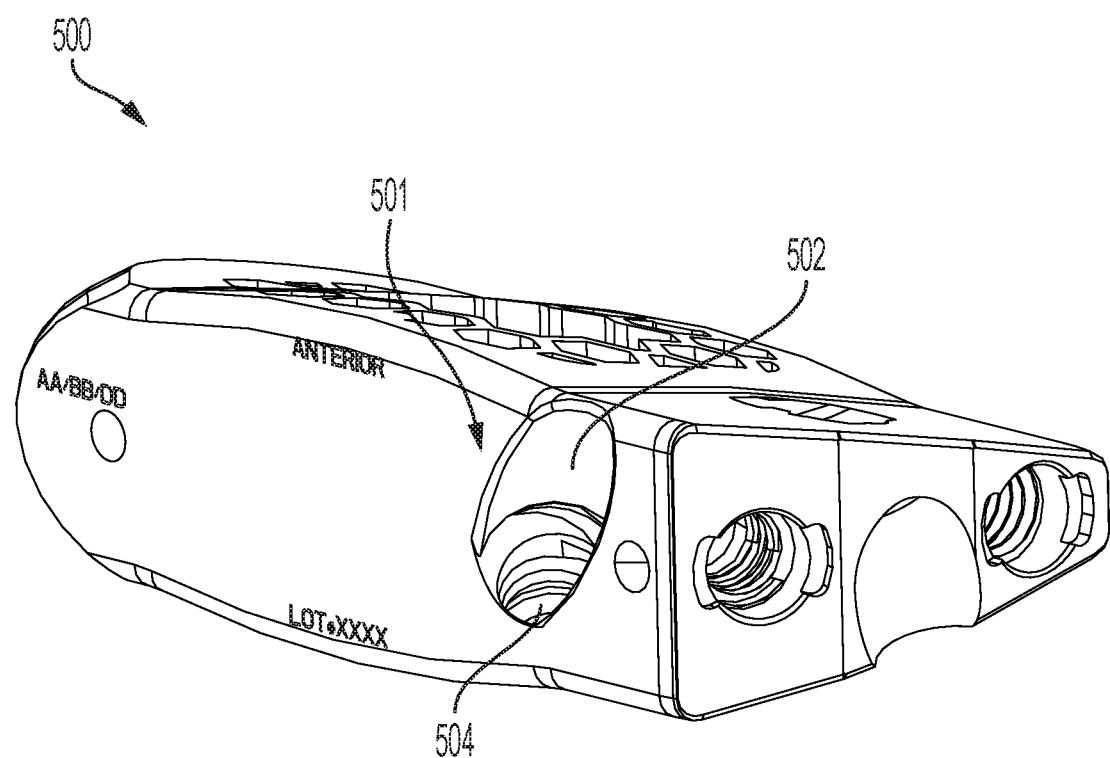
FIG. 5 illustrates a perspective view of a medical implant.

In one or more cases, the angled guide 106 may include a nested end 406 configured to be positioned within a medical implant 500, for example but not limited to an intervertebral fusion implant device, shown in FIG. 5. The medical implant 500 may include one or more fastener holes, such as the receptacle 501, configured to receive a portion of the angled guide 106 and a fastener therein, in order to fasten the medical implant 500 to, for example, a vertebra of a patient. The receptacle 501 may include one or more recesses, each sized to a diameter of a respective nested portion of the nested end 406. For example, the nested end 406 may include a first nested portion 407a and a second nested portion 407b. In one or more cases, the first nested portion 407a may include a proximal end 409 of the angled guide 106 and a tapered portion 411 of the angled guide 106. The proximal end 409 may be a rigid tubular member integrally formed with the outer shaft 102. The tapered portion 411 may be formed in a conical shape that tapers from the outer shaft 102 to proximal end 409 of the first nested portion 407a. The tapered portion 411 may facilitate the translation of the pivotal device 127 between the retracted position 401 and the deployed position 403. In one or more other cases, the first nested portion 407a may include only the proximal end 409, in which case the proximal end 409 may have the same diameter of the outer shaft 102 and a diameter that is greater than the diameter of the second nested portion 407b. The second nested portion 407b includes a proximal end 415 and a tapered portion 413. The proximal end 415 may be a rigid tubular member integrally formed with the outer shaft 102. The tapered portion 413 may be formed in a conical shape that tapers from the proximal end 409 to proximal end 415 of the second nested portion 407b. The tapered portion 413 may facilitate the translation of the pivotal device 127 between the retracted position 401 and the deployed position 403. The receptacle 501 of the medical implant 500 may include, for example, a first recess 502 and a second recess 504. The first recess 502 may have a mating diameter with the first nested portion 407a, and the second recess 504 may have a mating diameter with the second nested portion 407b. For the cases in which the nested end 406 is positioned within the receptacle 501, the first nested portion 407a may be seated within the first recess 502, and the second nested portion 407b may be seated within the second recess 504.

Figure 4D:
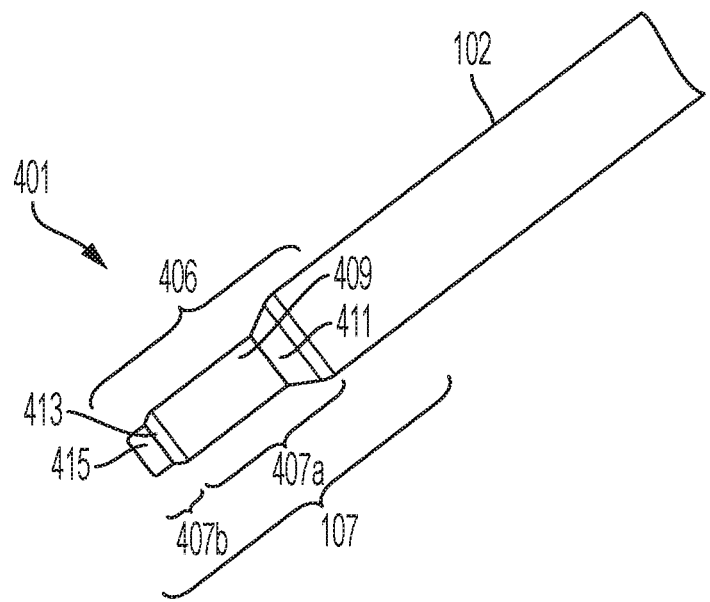
FIG. 4D illustrates an alternative guide for the medical access device of FIG. 1A in a retracted position.
Figure 4E:
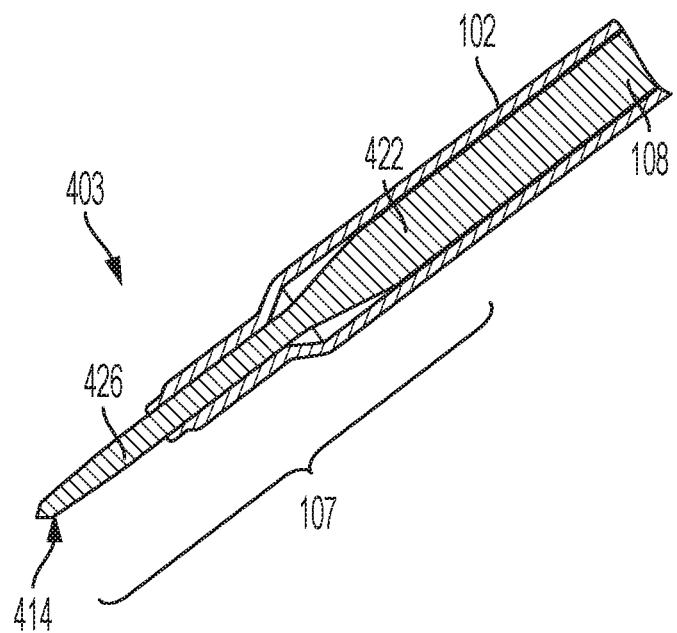
FIG. 4E illustrates a cross-sectional view of the alternative guide of FIG. 4D in a deployed position.

In one or more other cases, the device 100 includes a straight guide 107, as shown in FIGS. 4D and 4E and as opposed to the angled guide 106 as shown in FIGS. 4A-4C. It is noted that the straight guide 107 includes one or more of the same or similar features as the angled guide 106. These features are indicated with like drawing reference numbers. Accordingly, a description of such features is not repeated. Moreover, for the cases in which the device 100 utilizes the straight guide 107, the inner shaft 108 may include an access tool 426, such as an awl tip, that is rigidly coupled to a proximal end 422 of the inner shaft 108. The access tool 426 may be employed, for example but not limited to, to create an access hole within a section of spine or other bony structure of a patient. It is noted that the medical access device 300 may also utilize the straight guide 107 as opposed to the angled guide 106.

The outer shaft 102 may include the handle 104 disposed on or adjacent to the second end 129 of the outer shaft 102. The handle 104 may provide an ergonomic grip for a user to grasp the device 100. An outer housing 116 may be attached to the second end 129 of the outer shaft 102. In one or more cases, the outer housing 116 is manufactured with the outer shaft 102, forming a monolithic body. In one or more other cases, the outer housing 116 is coupled to the outer shaft 102 via welding or threading a portion of the outer housing 116 to a portion of the outer shaft 102. The outer housing 116 may be configured to house at least a portion of the knob 110 therein, such that the knob 110 may move in directions A and B. The outer housing 116 may include one or more pin tracks 118 configured to receive a pin 114 and guide the pin 114 as the knob 110 moves in directions A and/or B. The pin track 118 may be a recessed groove within the wall of the outer housing 116. For the cases in which the knob 110 utilizes multiple pins, the outer housing 116 includes an equal number of pin tracks each positioned to receive a pin protruding from the knob 110.

An external lever 112 may be pivotably coupled to an outer surface of the outer housing 116. The external lever 112 may be formed in a "U"-like shape or "V"-like shape, having two coupling ends 133 disposed on each end of the external lever 112 and connected to a middle portion 137 of the external lever 112. The middle portion 137 of the external lever 112 may be a rigid body, in which a curved portion of the body wraps around the outer housing 116 into two arms 147 that extend on either side of the outer housing towards the two coupling ends 133. The outer housing 116 includes a channel 149 disposed on a bottom end 139 of the outer housing 116, in which the channel 149 includes a bore that extends transversely across the outer housing 116. The two coupling ends 133 may be positioned on each end of the channel 149, and coupled to the channel 149 via a pin 131 inserted through the two coupling ends and the channel 149. The external lever 112 may be configured to rotate in directions C and I about the location where the two coupling ends 133 are coupled to the channel 149.

Figure 2A:
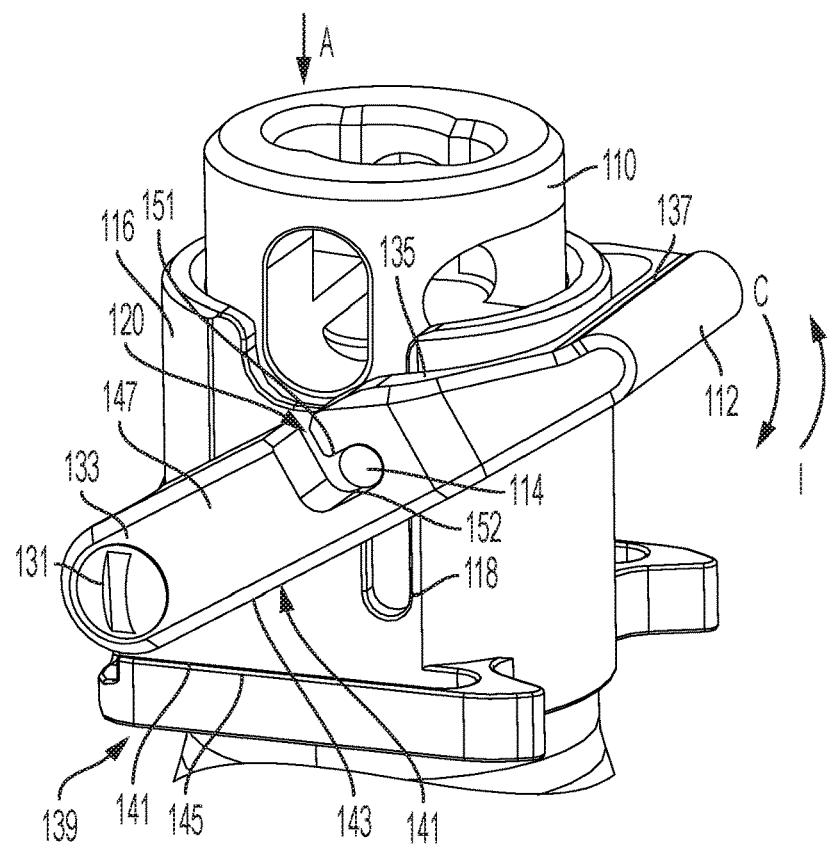
FIG. 2A illustrates a perspective view of an external lever of the medical access device in a retracted position.

The external lever 112 may be spring loaded, via at least one spring 141, in order to return the device 100 into a retracted position 401 after being moved into a deployed position 403, as shown in FIG. 2A. One portion of the spring 141 may be positioned within a recessed area 143 positioned on the underside of the arm 147, and another portion of the spring 141 may be positioned within a recessed area 145 on a bottom side 139 of the outer housing 116.

The external lever 112 may include a slot 120 positioned on the arm 147 of the external lever 112. The external lever 112 may include a slot 120 per pin 144 protruding from the knob 110. The surface 135 of the external lever 112 above the location of the slot 120 may be tapered towards the middle portion 137 of the external lever 112. The slot 120 may be formed in an "L" shape. A receiving portion 120b is a vertical pin track portion of the slot 120, and a locking portion 120a is a horizontal pin track portion of the slot 120. The receiving portion 120b may be configured to receive the pin 114 when the knob 110 is inserted into the outer housing 116 and to allow the knob 110 to exit the outer housing 116. The locking portion 120a may be configured to prevent the knob 110 from completely exiting the outer housing 116. In the retracted position 401, the pin 114 may be positioned within the locking portion 120a, and the locking portion 120a may be aligned with the pin track 118. In the deployed positioned 403, the pin 114 may be positioned within the receiving portion 120b, and the receiving portion 120b may be aligned with the pin track 118.

Figure 2B:
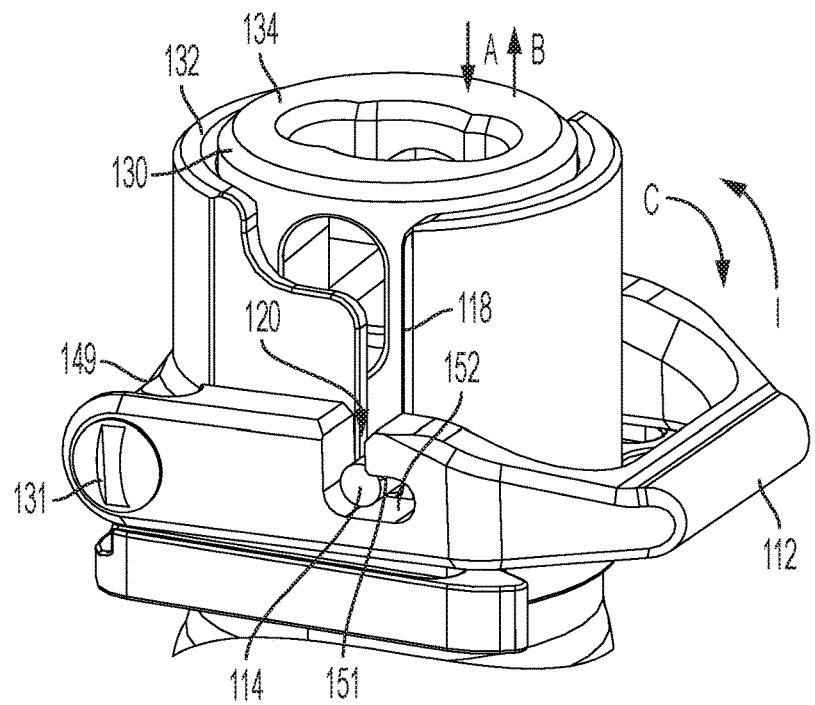
FIG. 2B illustrates a perspective view of the external lever of the medical access device in a deployed position.

FIG. 2A illustrates a perspective view of the external lever 112 of the device 100 in the retracted position 401. FIG. 2B illustrates a perspective view of the external lever 112 of the device 100 in the deployed position 403.

When the knob 110 is inserted into the outer housing 116 in the direction A, the pin 114 may contact and move smoothly across the tapered surface 135 of the external lever 112, thereby forcing the external lever 112 downwards in the direction C. As the pin 114 slides across the surface 135, the external lever 112 moves downwards in the direction C, and the pin 114 moves into the receiving portion 120b of the slot 120 and into the pin track 118 in the direction A. As the pin 114 moves farther down into the pin track 118, the pin 114 moves into the locking portion 120a, such the pin 114 moves beneath the upper surface 151 of the locking portion 120a, thereby locking the knob 110 into the outer housing 116. The spring 141 may bias the external lever 112 upwards into the retracted position 401. As the external lever 112 moves upwards, the bottom surface 152 of the slot 120 contacts the pin 114 in a direction B, thereby forcing the inner shaft 102, via the pin 114 coupled to the knob 110, upwards into the retracted positioned 401.

During a procedure, such as a fusion surgery, a user may position an implant 500 between two vertebrae, such as vertebra 602 and 604. Having positioned the implant 500, the user may insert the device 100 into a patient in a retracted position 401. For example, the user may insert the device 100 into an area of the patient ranging from an anterior side of the patient to a lateral side of the patient, and more preferably an anterolateral portion of the patient. The user may position the device 100 such that the pivotal device 127 is positioned at an angle to enter a top portion 604a, such as an endplate, of a vertebra, such as vertebra 604, as shown in FIG. 6A. The user may position the nested end 406 of angled guide 106 into the receptacle 501 of the implant 500, as shown in FIG. 6A. The user may strike the upper surface 134 of the knob 110 with an object, such as a mallet. As the knob 110 is struck, the knob 110 moves in the direction A, thereby moving the inner shaft 108 and the pivotal device 127 into the deployed position 403, as shown in FIG. 6B. In the deployed position 403, the access tool 126, for example an awl tip, of the pivotal device 127 punctures the vertebra 604, thereby creating an access hole in the vertebra 604. In one or more cases, the access tool 126 may be an elongated rod having a pointed tip on an insertion end 414 of the access tool 126. The spring 141 may bias the external lever 112, and thus the inner shaft 102, via the pin 114 coupled to the knob 110, upwards into the retracted positioned 401, such that the access tool 126 is not located within the vertebra 604. The user may remove the device 100 from the patient, and may insert a fastener into the receptacle 501 and the hole in the vertebra 604, thereby fastening the implant 500 to the vertebra 604. It should be noted that the receptacle 501 may be positioned within the implant 500, such that an access hole may be created in the vertebra 602 in a same or similar manner as the access hole created in the vertebra 604.

To remove the inner shaft 108 from the outer shaft 102, the user may rotate the external lever 112 in the direction C into a fully deployed position 403, such that the receiving portion 120b of the slot 120 aligns with the pin track 118. In the fully deployed position 403, the user may grasp the knob 110 and pull the knob 110 in the direction B until the inner shaft 108 is removed from the outer shaft 102.

Figure 3B:
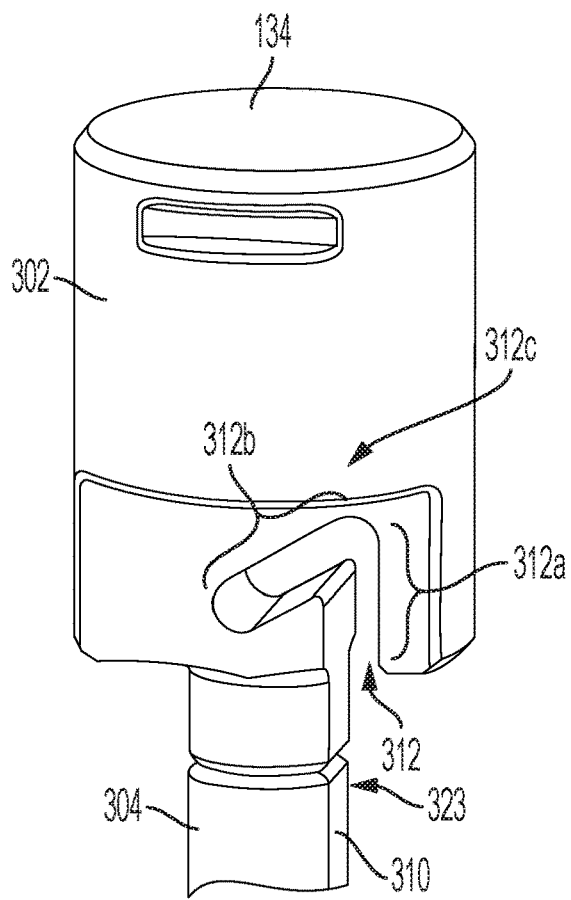
FIG. 3B illustrates a slot positioned on a knob of an inner shaft of the medical access device of FIG. 3A.
Figure 3C:
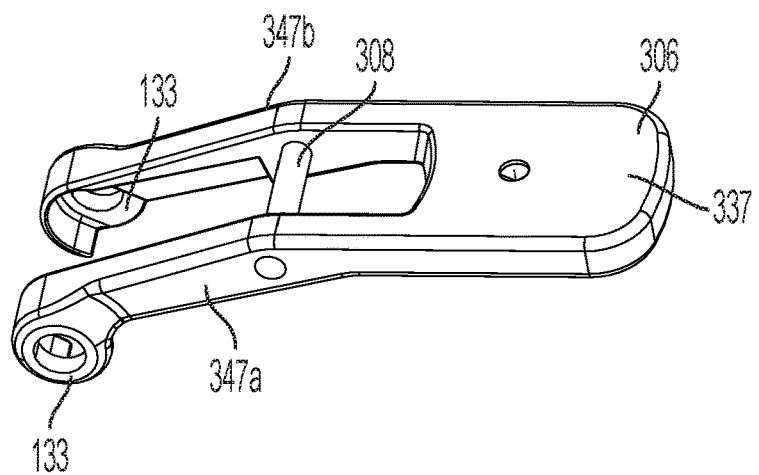
FIG. 3C illustrates an internal lever of the medical access device of FIG. 3A.
Figure 3D:
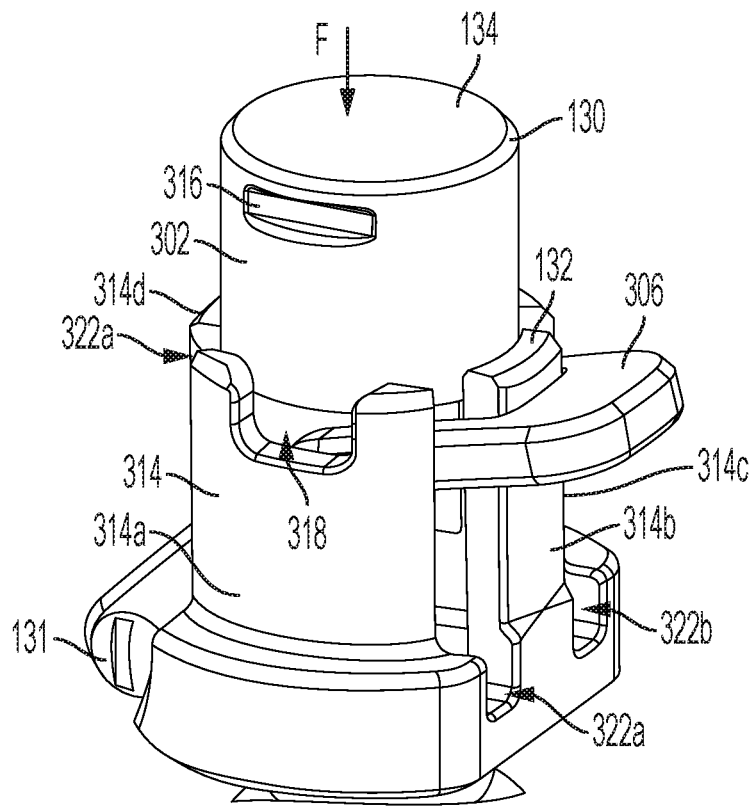
FIG. 3D illustrates a perspective view of the internal lever of the medical access device in a retracted position.
Figure 3E:
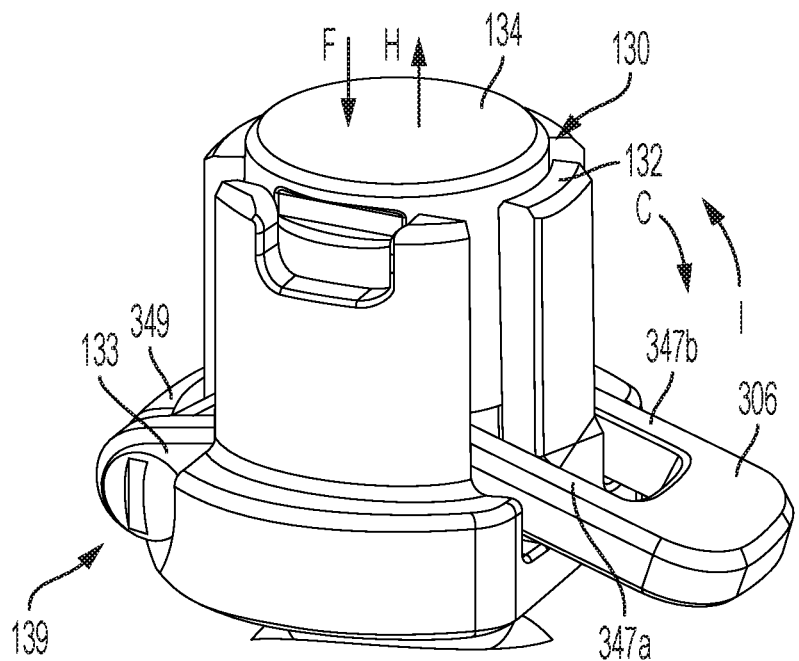
FIG. 3E illustrates a perspective view of the internal lever of the medical access device in a deployed position.

FIG. 3A illustrates a perspective view of another medical access device 300 (hereinafter the "device 300"). FIG. 3B illustrates a slot 312 positioned on a knob 302 of an inner shaft 304 of the device 300 of FIG. 3A. FIG. 3C illustrates an internal lever 306 of the device 300 of FIG. 3A. FIG. 3D illustrates a perspective view of the internal lever 306 of the device 300 in the retracted position 401. FIG. 3E illustrates a perspective view of the internal lever 306 of the device in the deployed position 403. It is noted that the device 300 includes one or more of the same or similar features as the device 100. These features are indicated with like drawing reference numbers. Accordingly, a description of such features is not repeated.

In one or more cases, the device 300 may be employed, for example, with an open or mini-open, minimal access and/or minimally invasive technique including, for example, a percutaneous surgical technique to create an access hole for a fastener at a surgical site within a body, for example, a section of a spine of a patient.

The device 300 includes the outer shaft 102 configured to receive the inner shaft 304. The inner shaft 304 may positioned within the outer shaft 102, and may be configured to translate through the outer shaft 102 along the axis $L_1$. The inner shaft 304 may have one or more of the same or similar features as the inner shaft 108. Additionally, the inner shaft 304 may include a keyed edge 310 configured to interlock with a pin 308 extending transversely across an internal lever 306. The keyed edge 310 may be a flat surface that extends along the axis $L_1$, whereas the remaining surface of the inner shaft 304 is cylindrically formed. For example, the outer perimeter of the inner shaft 304 may be formed in a "D" shape, in which the keyed edge 310 is the flat portion of the D-shaped perimeter. The keyed edge 310 may be used to orient the inner shaft 304 to be properly inserted into the outer shaft 102 by aligning the keyed edge 310 with the pin 308 of the internal lever 306. In one or more cases, the keyed edge 310 may extend along the axis $L_1$ of the first portion 107 of the inner shaft 304 for the entire length of the first portion 107. In one or more other cases, the keyed edge 310 may extend along at least a portion of the axis $L_1$ of the first portion 107.

The second end 323 of the inner shaft 304 may be fixedly coupled to a knob 302. In one or more cases, the second end 323 of the inner shaft 304 may be fixedly coupled to the knob 302 in a same or similar manner as the second end 123 of the inner shaft 108 being fixedly coupled to the knob 110. Accordingly, a description of such features is not repeated.

The upper surface 134 of the knob 302 may be a flat surface configured to receive one or more strikes from another object, such as a mallet, hammer, or other like instrument. The knob 302 may translate the force from the strike to the pivotal device 127 and into another object such as a vertebra 604, as shown in FIG. 6B. That is, the device 300 may translated the linear force from the strike on the knob 302 into an angular force when the pivotal device 127 in inserted into another object at an angle. The force from the strike may also cause the inner shaft 304 to move through the outer shaft 102. In a fully deployed position 403, the upper surface 134 may be elevated by a distance 130 from the upper surface 132 of the outer housing 314, as shown in FIG. 3E. By having the upper surface 134 elevated from the upper surface 132 in a fully deployed position 403, the object, such as the mallet, is prevented from contacting the upper surface 132 and translating the force of the strike into the outer shaft 102.

The knob 302 may include a slot 312 configured to receive the pin 308 positioned on the internal lever 306. The slot 312 may include a vertical track 312a interfaced with a diagonal track 312b. In one or more cases, the slot 312 may interface with the keyed edge 310, such that a flat surface of the keyed edge 310 aligns with a flat surface of the vertical track 312a. The vertical track 312a may be positioned on the same side of the inner shaft 304 as the keyed edge 310. The diagonal track 312b may interface with a top portion of the vertical track 312a and may slope at a downward angle away from the keyed edge 310.

An outer housing 314 may be attached to the second end 129 of the outer shaft 102. The outer housing 314 may be attached to the outer shaft 102 in a same or similar manner as attaching the outer housing 116 to the outer shaft 102. Accordingly, a description of such features is not repeated. The outer housing 314 is configured to house at least a portion of the knob 302 therein, such that the knob 302 may move in directions F and H. The outer housing 314 may include at least two tracks, such as track 322a and 322b, that allow the internal lever 306 to translate through the outer housing 314. To accommodate two tracks, a portion of the outer housing 314 may be separated into four walls, in which three walls define one track. For example, track 322a may be defined by wall 314a, 314d, and 314b, and track 322b may be defined by wall 314c, 314b, and 314d. An arm of the internal lever 306 may move within a track. For example, the arm 147a of the internal lever 306 may move within track 322a, and the arm 147b of the internal lever 306 may move within the track 322b.

The internal lever 306 may be pivotably coupled to an outer surface of the outer housing 314. The internal lever 306 may be formed in a "U"-like shape, having two coupling ends 133 disposed on each end of the arms 147a and 147b of the internal lever 306. The arms 147a and 147b may be connected via a middle portion 337 of the internal lever 306. The middle portion 337 of the internal lever 306 may be a rigid body, in which a curved portion of the body wraps around the wall 314b of outer housing 314 into the two arms 147a and 147b. The outer housing 314 includes a channel 349 disposed on a bottom end 139 of the outer housing 314, in which the channel 349 includes a bore that extends transversely across the outer housing 314. The two coupling ends 133 may be positioned on each end of the channel 349, and coupled to the channel 349 via a pin 131 inserted through the two coupling ends 133 and the channel 349. The internal lever 306 may be configured to rotate in directions C and I about the location where the two coupling ends 133 are coupled to the channel 349. The internal lever 306 includes the pin 308, in which one end of the pin 308 is attached to the arm 147a and the opposite end of the pin 308 is attached to the arm 147b. The pin 308 may be configured to move within the slot 312. In one or more cases, the internal lever 306 may be spring loaded to return the device 300 to the retracted position 401, in a same or similar manner as the spring loaded external lever 112. Accordingly, a description of such features is not repeated.

To initially insert the inner shaft 304 into the outer shaft 102, the inner shaft 304 is positioned within the outer shaft 102. As the inner shaft 304 slides into the outer shaft 102 in the F direction, the pin 308 of the internal lever 306 enters the vertical track 312a of the slot 312. When the pin 308 reaches the top portion 312c of the vertical track 312a, the spring 141 biases the internal lever 306 upwards and into the diagonal track 312b, thereby locking the inner shaft 304 with the outer shaft 102 and preventing the inner shaft 304 from completely exiting the outer shaft 102. While locked with the outer shaft 102, the device 300 may move between the retracted position 401 and the deployed position 403. To move the device 300 into the deployed position 403, the knob 302 moves in the F direction. While moving in the F direction, the pin 308 may slide upwards within the diagonal track 312b, and then downwards into the vertical track 312a. When the device 300 is moved from the deployed position 403 to the retracted position 401, the pin 308 contacts a portion of the slot 312, and the biasing force of the spring 141 forces of the knob 302 upwards in the H direction and into the retracted position 401. To remove the inner shaft 302 from the outer shaft 102, the user moves the device 300 to a completely deployed position 403, holds the internal lever 306 downwards in the C direction, and while grasping a portion of the knob 302, removes the knob 302 in the H direction until the inner shaft 304 is removed from the outer shaft 102.

In one or more embodiments, the devices 100 and 300 and implant 500 of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one or more embodiments, the devices 100 and 300 and implant 500 of the present disclosure may be employed with other spine or bone related applications, including those associated with diagnostics and therapeutics. In one or more embodiments, the disclosed devices 100 and 300 and implant 500 may be employed in a surgical treatment with a patient in a prone or supine position, and/or employ various surgical approaches to the spine, including anterior, posterior, posterior midline, direct lateral, posterolateral, and/or anterolateral approaches, and in other body regions. The devices 100 and 300 and implant 500 of the present disclosure may be employed with procedures for treating the lumbar, cervical, thoracic, sacral and pelvic regions of a spinal column. The system of the present disclosure may also be used on animals, bone models and other non-living substrates, such as, for example, in training, testing and demonstration. The devices 100 and 300 may be assembled for a surgical procedure, disassembled post-surgical procedure for cleaning, sterilization and maintenance purposes, and re-assembled for use in another surgical procedure. In one or more other embodiments, the devices 100 and 300 may be employed to create an access hole for other types of orthopedic surgeries, such as, but not limited to, foot, ankle, shoulder, elbow, and/or hand surgeries.

The components of the devices 100 and 300 and the implant 500 can be fabricated from biologically acceptable materials suitable for medical applications, including metals, plastics, synthetic polymers, ceramics and bone material and/or their composites. For example, the components of the devices 100 and 300, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan). In another example, the implant 500 may be, individually or collectively, fabricated from thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the devices 100 and 300 and the implant 500 may have material composites, including the above materials, to achieve various desired characteristics such as strength, rigidity, elasticity, compliance, biomechanical performance, durability and radiolucency or imaging preference. The components of devices 100 and 300 and implant 500, individually or collectively, may also be fabricated from a heterogeneous material such as a combination of two or more of the above-described materials. The components of devices 100 and 300 and implant 500 may be monolithically formed, integrally connected or include fastening elements and/or instruments, as described herein.

As used herein, the term "about" in reference to a numerical value means the numerical value with which it is being used or a numerical value within a range of plus or minus 10% of the numerical value of the number with which it is being used.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A surgical device comprising:
   a tubular outer shaft having a longitudinal axis and an angled guide positioned on a first end of the tubular outer shaft, the angled guide being angled relative to the longitudinal axis of the tubular outer shaft;
   an elongated inner shaft having a second end and a third end, the elongated inner shaft being removably coupled to the tubular outer shaft and configured to axially translate through the tubular outer shaft, the elongated inner shaft further comprising a knob disposed on the second end of the elongated inner shaft and being configured to axially translate within a housing positioned on a fourth end of the tubular outer shaft opposite the first end;
   at least one pin protruding from an outer surface of the knob;
   at least one track positioned within the housing and configured to guide the at least one pin as the knob axially translates within the housing;
   an external lever having at least one end pivotally coupled to an outer surface of the housing and at least one slot removably coupled to the at least one pin, thereby securing the elongated inner shaft to the tubular outer shaft; and
   a pivotal device having at least one joint and a piercing tool, the piercing tool being configured to puncture a portion of a bone,
   wherein the at least one joint is pivotally coupled to the third end of the elongated inner shaft and to an end of the piercing tool, and
   wherein the pivotal device is configured to axially translate through the angled guide into a deployed position.

2. The surgical device of claim 1,
   wherein the knob is configured to receive a strike from an object and move the pivotal device from a retracted position to the deployed position.

3. The surgical device of claim 1, wherein the surgical device is configured to translate a linear force, generated by a strike to the second end of the elongated inner shaft, to an angular force when the pivotal device is axially translated through the angled guide.

4. The surgical device of claim 1, wherein the piercing tool is an awl.

5. The surgical device of claim 1, wherein an insertion end of the angled guide is nested and configured to fit within a fastening hole of an implant having a shape corresponding to the insertion end of the angled guide.

6. The surgical device of claim 5, wherein a first portion of the insertion end comprises a tubular shape having a first diameter, and a second portion of the insertion end comprises a tubular shape having a second diameter smaller than the first diameter.

7. A surgical device comprising:
   a tubular outer shaft having a longitudinal axis in which an angled guide is positioned on a first end of the tubular outer shaft and a housing is positioned on a second end of the tubular outer shaft opposite to the first end, the angled guide being angled relative to the longitudinal axis of the tubular outer shaft;
   an elongated inner shaft having a third end and a fourth end, the elongated inner shaft being removably coupled to the tubular outer shaft and configured to axially translate through the tubular outer shaft;
   a pivotal device having at least one joint and a piercing tool, the piercing tool being configured to puncture a portion of a bone,
   wherein the at least one joint is pivotally coupled to the fourth end of the elongated inner shaft and to an end of the piercing tool, and
   wherein the pivotal device is configured to axially translate through the angled guide into a deployed position;
   a knob disposed on the third end of the elongated inner shaft;
   at least one pin protruding from an outer surface of the knob;
   at least one track positioned within the housing and configured to guide the at least one pin as the knob axially translates within the housing; and
   an external lever having at least one end pivotally coupled to an outer surface of the housing and at least one slot removably coupled to the at least one pin, thereby securing the elongated inner shaft to the tubular outer shaft.

8. The surgical device of claim 7, wherein the knob is configured to receive a strike from an object and move the pivotal device from a retracted position to the deployed position.

9. The surgical device of claim 7, wherein the surgical device is configured to translate a linear force, generated by a strike to the third end of the elongated inner shaft, to an angular force when the pivotal device axially translated through the angled guide.

10. The surgical device of claim 7, wherein the access piercing tool is an awl.

11. The surgical device of claim 7, wherein an insertion end of the angled guide is nested and configured to fit within a fastening hole of an implant having a shape corresponding to the insertion end of the angled guide.

12. The surgical device of claim 11, wherein a first portion of the insertion end comprises a tubular shape having a first diameter, and a second portion of the insertion end comprises a tubular shape having a second diameter smaller than the first diameter.

* * * * *